United States Patent
Matie

(10) Patent No.: US 11,090,205 B2
(45) Date of Patent: Aug. 17, 2021

(54) METHODS AND COMPOSITIONS FOR TREATMENT OF SKIN CONDITIONS

(71) Applicant: Matie Holdings, LLC, Plano, TX (US)

(72) Inventor: Michelle Matie, Plano, TX (US)

(73) Assignee: Matie Holdings LLC, Plano, TX (US)

( * ) Notice: Subject to any disclaimer, the term of this patent is extended or adjusted under 35 U.S.C. 154(b) by 0 days.

(21) Appl. No.: 16/362,600

(22) Filed: Mar. 22, 2019

(65) Prior Publication Data

US 2019/0240088 A1 Aug. 8, 2019

Related U.S. Application Data

(63) Continuation of application No. 12/446,946, filed as application No. PCT/US2007/022523 on Oct. 24, 2007, now abandoned.

(60) Provisional application No. 60/853,912, filed on Oct. 24, 2006.

(51) Int. Cl.

| A61K 8/9789 | (2017.01) |
|---|---|
| A61K 8/9794 | (2017.01) |
| A61K 8/60 | (2006.01) |
| A61F 15/00 | (2006.01) |
| A61Q 19/08 | (2006.01) |
| A61K 8/67 | (2006.01) |
| A61Q 19/00 | (2006.01) |
| A61Q 17/04 | (2006.01) |

(52) U.S. Cl.
CPC ............... *A61F 15/00* (2013.01); *A61K 8/60* (2013.01); *A61K 8/676* (2013.01); *A61K 8/9789* (2017.08); *A61K 8/9794* (2017.08); *A61Q 19/08* (2013.01); *A61Q 17/04* (2013.01); *A61Q 19/007* (2013.01); *A61Q 19/008* (2013.01)

(58) Field of Classification Search
CPC combination set(s) only.
See application file for complete search history.

(56) References Cited

U.S. PATENT DOCUMENTS

| 5,494,657 A * | 2/1996 | Swenson ................. A61K 8/925 424/59 |
|---|---|---|
| 6,011,067 A | 1/2000 | Hersh |
| 6,669,932 B2 | 12/2003 | Imanaka et al. |
| 2001/0055597 A1 | 12/2001 | Liu et al. |
| 2002/0028844 A1* | 3/2002 | Fitzpatrick ............. A61K 31/20 514/474 |
| 2003/0059450 A1* | 3/2003 | Maibach ................. A61K 8/19 424/401 |
| 2004/0192649 A1 | 9/2004 | Bissett et al. |
| 2004/0219115 A1 | 11/2004 | Kini et al. |
| 2005/0202103 A1 | 9/2005 | Rajendran et al. |
| 2006/0018851 A1* | 1/2006 | Patt .......................... A61K 8/19 424/62 |

FOREIGN PATENT DOCUMENTS

WO 9834591 A1 8/1998

OTHER PUBLICATIONS iam health.com, "Bamboo Sil 180 caps", Product Sheet, (Feb. 1, 2006), URL: http://www.i-am-health.com/model/320, XP008109071.

* cited by examiner

*Primary Examiner* — Jared Barsky
(74) *Attorney, Agent, or Firm* — Hubbard Johnston, PLLC

(57) ABSTRACT

Topical skin care compositions are described that include effective amounts of anti-inflammatory, antioxidant, silica and sugar compounds. In addition, methods of treating skin conditions are described, which include applying topically to a site of treatment a therapeutically effective amount of a composition comprising anti-inflammatory, antioxidant, silica and sugar compounds.

2 Claims, No Drawings

METHODS AND COMPOSITIONS FOR TREATMENT OF SKIN CONDITIONS

CROSS REFERENCES TO RELATED APPLICATIONS

This Application is a Continuation of U.S. patent application Ser. No. 12/446,946, filed Dec. 10, 2009, which is a National Stage Entry under 35 U.S.C. 371, filed Oct. 24, 2007, which claims the benefit of U.S. Provisional Application 60/853,912, filed Oct. 24, 2006, all of which are included herein by reference in their entirety.

TECHNICAL FIELD OF THE INVENTION

The invention relates to skincare compositions, as well as methods for the treatment of a variety of skin conditions. Compositions of the invention include effective amounts of a sugar compound, an anti-inflammatory component, an antioxidant component and a silica component.

BACKGROUND OF THE INVENTION

Human skin is a composite material of the epidermis and the dermis. The principal functions of the skin include protection, excretion, secretion, absorption, thermoregulation, pigmentogenesis, accumulation, sensory perception, and regulation of immunological processes. These functions are detrimentally affected by the structural changes in the skin due to aging and excessive sun exposure.

The mechanical properties of the skin, such as elasticity, are controlled by the density and geometry of the network of collagen and elastic fiber tissue therein. Damaged collagen and elastin lose their contractile properties, resulting in skin wrinkling and skin surface roughness. As the skin ages or becomes unhealthy, it acquires sags, stretch marks, bumps, bruises or wrinkles, it roughens, and it has reduced ability to synthesize Vitamin D. Aged skin also becomes thinner and has a flattened dermoepidermal interface because of the alterations in collagen, elastin, and glycosaminoglycans.

Human skin is subjected to numerous environmental and other conditions. Some of these environmental conditions, such as sunburn irritate the skin. In addition, the use of skin exfoliants such as the hydroxy acids, as well as other cosmetic compounds used to diminish skin lines and wrinkles, oftentimes irritates the skin. Therefore, it would be useful to provide topical composition to address these and other skin irritants.

A variety of vitamins and minerals have individually been administered to treat certain skin and other problems that occur when the patient has a deficiency of that vitamin or mineral. Vitamin A, for example, assists in the treatment of acne and to facilitate wound healing; vitamin C (ascorbic acid) assists in the prevention of skin bruising and wound healing; vitamin E is an antioxidant; and copper assists in the treatment of elastic tissue defects. Topical use of vitamin C is also believed to ward off sun damage, reduce breakdown of connective tissues, and possibly promote collagen synthesis. Vitamin E is used topically as an anti-inflammatory agent, for enhancement of skin moisturization, for UV-ray protection of cells, and for retardation of premature skin aging.

It is desired to find a topical composition for application to human skin where the composition serves as an antioxidant, as an anti-inflammatory and controls wrinkles. In addition, it is desirable to find a skin care composition that also effectively treats conditions such as sensitive eyes, blepharitis (inflammation of the eyelid), rosacea, atopic dermatitis and seborreheic dermatitis in human subjects. The present invention advantageously provides compositions, as well as methods of treatment comprising the administration of the above compositions, to repair skin for the prevention and treatment of wrinkles and other skin disorders.

SUMMARY OF THE INVENTION

The present invention relates to a topical composition for the prevention and treatment of skin conditions in a patient comprising at least one anti-inflammatory component, at least one antioxidant component in an amount sufficient to negate the effect of free radicals, and at least one moisturizing agent.

In one embodiment, the antioxidant component is present at about 0.05 to 5%, the anti-inflammatory component is present at about 0.05 to 5% of the composition, and the moisturizing agent is present at 5 to 30%.

In another embodiment of the invention, the skin care compositions of the invention further comprise one or more of a thickener, humectant, preservative, emulsifier and pH balancer.

In one embodiment according to the invention, the skin condition treated is at least one of wrinkles, fine lines, thinning, reduced skin elasticity, reduced skin moisture, spider veins, senile purpura, sun damaged skin, aging skin, or rough skin. In a preferred embodiment, the composition is administered as a lotion. Other forms of administration of the compositions of the invention include a spray, ointment, balm, or cream.

In another embodiment, the composition is administered in conjunction with concurrent or subsequent treatment by at least one additional pharmaceutical or non-pharmaceutical composition for the prevention or treatment of a skin condition.

DETAILED DESCRIPTION OF EXEMPLARY EMBODIMENTS

All weights, measurements and concentrations herein are measured at 25° C., unless otherwise specified. Unless otherwise indicated, all percentages of compositions referred to herein are weight percentages of the total composition (i.e. the sum of all components present) and all ratios are weight ratios. Except where specific examples of actual measured values are presented, numerical values referred to herein should be considered to be qualified by the word "about".

The lipophilic phase according to compositions of the invention may comprise any material that is liquid at ambient conditions and is substantially water-insoluble; any material that is solid at ambient conditions, has a melting temperature of less than 100.degree. C. and melts to form a water immiscible liquid; or mixtures of such materials.

The hydrophilic phase of the inventive composition includes water in an amount to provide a desired consistency for the product. In one embodiment, the personal skin care composition contains water in an amount preferably between 50% to 80% by weight. Additionally, this amount of water can be increased or decreased as desired.

An embodiment of the invention includes a lipophilic phase that is prepared and combined with a hydrophilic phase.

A composition of the invention aids in the reduction of wrinkles and the improvement of other skin conditions, such as increased skin elasticity and skin softness. Moreover, the prevention or treatment of unhealthy skin, such as aged skin or skin overexposed to sunlight, may advantageously be accomplished by the administration of the compositions of the present invention to a human in need of treatment. The pharmaceutical composition includes the combination of a number of different components that interact to provide the desired improvements to the skin.

The compositions of the invention prevent and improve skin conditions by using sufficient amounts of at least one anti-oxidant agent, at least one anti-inflammatory agent and at least one moisturizing agent. Antioxidants, such as ascorbate and the compounds contained in pea extract, inhibit collagenase and elastase, enzymes that break down collagen and elastic tissues. These antioxidants assist in the prevention of additional wrinkles and facilitate the healing of skin tissues. Anti-inflammatory components are included to reduce inflammation, swelling, itching and redness of skin. Moisturizing agents are used to maintain the skin in a soft and healthy state.

Additionally, compositions of the invention control wrinkles, increase synthesis of collagen and restore the surface of the skin.

The antioxidant component is preferably present in an amount of about 0.05 to 5%, more preferably about 0.1 to 1%, and most preferably about 0.5 weight percent of the composition.

The composition includes at least one antioxidant, which typically is a vitamin C source and preferably is ascorbic acid, or a pharmaceutically acceptable salt or ester thereof, and more preferably is ascorbyl palmitate, dipalmitate L-ascorbate, sodium L-ascorbate-2-sulfate, tetrahexyldecyl ascorbate or an ascorbic salt, such as sodium, potassium, or calcium ascorbate, or mixtures thereof. The vitamin C source is present in the pharmaceutical composition in about 0.05 to 5%, and preferably about 0.5%.

The composition optionally includes an additional antioxidant component derived from pea extract. The extract of *Pisum sativum* also contains essential amino acids and proteins that assist in the production of collagen and elastin.

The composition also includes a silica component. The silica component is usually derived from a rich natural source of silica such as bamboo. Additional natural sources of silica include the extract of the horsetail plant. The use of a silica component stimulates chondroblasts to produce chondroitin and hyaluronic acid, which in turn provide strength and resilience to collagen and elastin.

The anti-inflammatory component is preferably present in about 0.05 to 5%, and most preferably present at about 1% of the composition. In an embodiment of the invention, the anti-inflammatory component is derived from licorice extract.

Throughout this description and in the appended claims, the phrase "licorice extract" refers to any compound or combination of compounds in the glycyrrhiza family (i.e., *Glycyrrhiza glabra*), including glycyrrhiza, glycerrhetic acid (also known as "enoxolone," "uralenic acid," and "glycyrrhetinic acid"), glycyrrhizic acid (also known as "glycyrrhizin," "glycyrrhizinic acid," and "glycyrrhetinic acid glycoside"), derivatives thereof, and combinations thereof. Presently preferred derivatives of licorice extracts include salts (e.g., metal salts, ammonium salts, and the like) and esters (e.g. saturated fatty acid esters, unsaturated fatty acid esters, diacid half esters, glycoside esters, and the like).

Preferred licorice extract ester derivatives include saturated and unsaturated esters of glycerrhetic acid and glycyrrhizic acid in which the ester portion of the molecule contains from 2 to 24 carbon atoms, more preferably from 10 to 24 carbon atoms, still more preferably from 16 to 24 carbon atoms. Representative licorice extract ester derivatives for use in accordance with the present invention include but are not limited to monoammonium glycyrrhizinate, monopotassium glycyrrhizinate, dipotassium glycyrrhizinate, 1-beta-glycyrrhetic acid, stearyl glycyrrhetinate, 3-stearyloxy-glycyrrhetinic acid, disodium 3-succinyloxy-beta-glycyrrhetinate, and the like. Dipotassium Glycyrrhizinate is a preferred licorice extract, and the dipotassium glycyrrhizinate sold under the tradename NET-DGT™ by Barnet Products Corporation (Englewood Cliffs, N.J.) is especially preferred.

Preferably, licorice extracts used in accordance with the present invention are present in an amount from about 0.05% to about 5% by weight of the composition. More preferably, the licorice extract is present in an amount about 1% by weight of the composition.

In certain of the presently preferred embodiments, it is desirable that the licorice extract is present in an amount of at least about 0.01 percent by weight of the composition, more desirably at least about 0.05 percent by weight of the composition, and still more desirably at least about 0.1 percent by weight of the composition. The presence of the licorice extract in an amount of about 1 percent by weight of the composition is particularly preferred at present.

Compositions embodying features of the present invention are effective in lowering background levels of both $PGE_2$ (Prostaglandin $E_2$), a biomarker of irritant-induced inflammation, and GM-CSF (Granulocyte-Macrophage Colony Stimulating Factor), a biomarker of immuno-induced inflammation. The efficacy of these compositions is similar to that of dexamethasone, a synthetic glucocorticoid that has long been used therapeutically as an immunosuppressive and as an anti-inflammatory agent. It is presently believed that the mechanism of action of compositions embodying features of the present invention may involve a regulatory effect exerted by licorice extract acting to modulate inflammatory response.

To prepare the compositions according to the present invention, the various components are mixed with a pharmaceutically or cosmetically acceptable vehicle or carrier. The cosmetically acceptable vehicle acts as a diluent, dispersant or carrier for other materials present in the composition, so as to facilitate their distribution when the composition is applied to the skin. Vehicles other than water can include liquid or solid emollients, solvents, humectants, thickeners and powders.

The pharmaceutically or cosmetically acceptable vehicle will usually form from about 10% to about 99.9%, preferably from about 50% to 99% by weight of the total composition, and can, in the absence of other cosmetic adjuncts or additives, form the balance of the composition. In an embodiment of the invention, the cosmetically acceptable vehicle into which the remaining ingredients are mixed, is deionized water.

An embodiment of the invention may include a composition comprising pea extract. The protein in pea extract improves skin tension, controls wrinkling and has film-forming and moisturizing properties.

The composition preferably contains at least one sugar compound, and more preferably just one sugar compound, present in about 0.05 to 5%, and preferably about 0.1% of the composition. In an embodiment of the invention, the sugar compound is glucosamine hydrochloride (glucosamine HCl). The sugar compound may be a compound that is capable of being converted to glycosaminoglycans in the human bloodstream, which in combination with other ingredients disclosed herein assists in thickening the dermis and supplementing collagen and elastic tissues. A thicker dermis desirably reduces the wrinkling and lines that occur when areas of the skin become thin.

The compositions of the inventions may also comprise one or preservatives. The role of a preservative in the composition is to prevent and control microbial growth. Preferred preservatives includes parabens such as methylparaben and propylparaben, or natural agents such as citrus compounds.

The compositions of the invention may comprise one or more humectant compounds. Humectants are hygroscopic and absorb moisture from the atmosphere. The presence of humectants in the compositions of the invention improves their moisturizing capabilities.

An embodiment of a composition of the invention may include an additional moisturizing agent. Such an agent may comprise hydrocarbon compounds such as squalene. As a topical, squalene is a non-greasy moisturizer that instantly softens the skin and helps prevent cell damage.

The compositions of the present invention may be formulated as a solution, gel, lotion, cream, ointment, oil-in-water emulsion, water-in-oil emulsion, stick, spray, ointment, paste, mousse, suppository, and the like or other pharmaceutically acceptable form. In addition, the compositions can be transferred to a site of inflammation from the gauze portion of an adhesive bandage.

The compositions of the present invention may also contain various known and conventional cosmetic ingredients so long as they do not detrimentally affect the desired effects provided by the combination of the components. For example, the composition of the present invention can further include one or more additives or other optional ingredients well known in the art, which can include but are not limited to fillers (e.g., solid, semi-solid, liquid, etc.); carriers; diluents; emollients; emulsifiers; surfactants; structuring agents; thickening agents; gelling agents; vitamins, retinoids, and retinols (e.g., vitamin $B_3$, vitamin A, etc.); pigments; fragrances; sunscreens and sunblocks; anti-oxidants and radical scavengers; organic hydroxy acids; desquamation agents; exfoliants; skin lightening agents; skin conditioners; moisturizers; ceramides, pseudoceramides, phospholipids, sphingolipids, cholesterol, hyaluronic acid and its derivatives, collagen synthesis promoters, glucosamine, pharmaceutically acceptable penetrating agents (e.g., n-decylmethyl sulfoxide, lecithin organogels, etc.); preservatives; antimicrobial agents; and the like; and combinations thereof.

An embodiment of the invention is directed to the treatment of a human subject in need thereof, with a therapeutically effective amount of a composition of the invention. The term "therapeutically effective amount" as used herein, refers to amounts of the compositions that are effective to reduce or prevent the ill-effects of the skin care conditions listed herein including but not limited to, sensitive eyes, blepharitis (inflammation of the eyelid), rosacea, atopic dermatitis and seborreheic dermatitis. Methods of treating skin conditions embodying features of the present invention include applying topically to an area of human skin an effective amount of a composition of a type described herein. The frequency at which topical applications in accordance with the present invention are performed is not limited, and may vary depending on the type and severity of the condition to be treated. In addition, the type and cause of inflammation to be treated by topically applying compositions embodying features of the present invention is not limited, and includes all types and causes of inflammation having a potential to benefit from contact with a composition in accordance with the present invention.

Inflammatory diseases that may be treated or prevented include, for example, septic shock, septicemia, and adult respiratory distress syndrome.

Compositions of the invention can also be used to heal wounds and are particularly beneficial for chronic wound healing. Additional uses of the compositions of the invention include their application in their treatment of necrosis of the skin and associated tissue, including reducing the inflammation association with necrosis.

The following examples further describe and demonstrate embodiments within the scope of the present invention. The examples are given solely for the purpose of illustration and are not to be construed as limitations of the present invention. Ingredients are identified by common/chemical name, INCI (International Nomenclature of Cosmetic Ingredients) name, or otherwise defined below. All amounts are percentages by weight based on the total composition weight.

TABLE 1

Anti-Oxidant/Anti-Inflammatory Compositions

| Phase | Ingredient | Ranges |
|---|---|---|
| 1 | Water | 50-80% |
| 1 | Carbomer | 0.05-5% |
| 1 | Butylene Glycol | 2-10% |
| 1 | Xanthan Gum | 0.05-5% |
| 1 | Methylparaben | 0.05-5% |
| 1 | Dipotassium Glycyrrhizinate | 0.05-5% |
| 2 | Tetrahexyldecyl Ascorbate | 0.05-5% |
| 2 | Nikkomulese-4 ™ | 0.05-5% |
| 2 | Squalene | 5-30% |
| 2 | Propylparaben | 0.05-5% |
| 3 | Triethanoelamine and water | 0.05-5% |
| 4 | Dermox ™ SRC | 0.005-1% |

The preparation of the hydrophilic phase (1) is as follows. The following ingredients are placed in a first vessel: water, carbomer, butylene glycol, xanthan gum, methylparaben and dipotassium glycyrrhizinate. The ingredients are heated in the first vessel to a temperature of approximately 80° C.

The preparation of the lipophilic phase (2) is as follows. The following ingredients are placed in a second vessel: tetrahexyldecyl ascorbate, Nikkomulese 41, squalene and propylparaben. The ingredients are heated in the second vessel to a temperature of approximately 70° C. and mixed until a uniform mixture is obtained.

The final composition is prepared by combining the mixture in the second vessel into the first vessel accompanied by propelling mixing. The phase 3 ingredients (triethanolamine and water) are added and propelling mixing is continued. The mixture is then allowed to cool to approximately 40° C.

After the mixture has cooled to approximately 40° C., the ingredient in phase 4 is added: Dermox SRC, which is a mixture of *Bambusa vulgaris* (common bamboo) extract, *Pisum sativum* (pea) extract and glucosamine hydrochloride. The mixture is mixed into an emulsion.

Although there has been described what is at present considered to be the preferred embodiments of the present personal skin care composition, it will be understood that the present personal skin care composition can be embodied in other specific forms without departing from the spirit or essential characteristics thereof. The present embodiments are, therefore, to be considered in all aspects as illustrative and not restrictive.

A skin care composition including from about 50% to about 70%, based on the total weight of the composition, of water; from about 0.10% to about 10.0%, based on the total weight of the composition, of a preservative; from about 0.10% to about 10%, based on the total weight of the composition, of a thickening agent; from about 0.05% to about 5%, based on the total weight of the composition, of a anti-inflammatory agent; from about 0.05% to about 5.0%, based on the total weight of the composition, of an emulsifying agent; from about 5% to about 30%, based on the total weight of the composition, of a moisturizing agent; from about 2% to about 10.0%, based on the total weight of the composition, of a humectant (attracts moisture from the atmosphere); from about 0.05% to about 5.0%, based on the total weight of the composition, of an anti-oxidant agent; from about 0.05% to about 5.0%, based on the total weight of the composition, of a pH balancer; and from about 0.005% to about 1%, based on the total weight of the composition, of a mixture consisting of *Bambusa vulgaris* (common bamboo) extract, *Pisum sativum* (pea) extract and glucosamine hydrochloride.

Preferably, the preservative is at least one preservative selected from the group consisting of methylparaben and propylparaben. Preferably, the thickening agent is at least one thickening agent selected from the group consisting of carbomer and xanthan gum. Preferably, the emulsifying agent is a water-in-oil emulsifier with a silicon touch, such as Nikkomulese 41. Preferably, the humectant is at least one humectant selected from the group consisting of butylene glycol, propylene glycol, glycerin and glyceryl triacetate. Preferably, the anti-oxidant agent is at least one anti-oxidant agent selected from the group consisting of tetrahexyldecyl ascorbate and vitamin C derivatives. Preferably, the anti-inflammatory agent is at least one anti-oxidant agent selected from the group consisting of dipotassium glycyrrhizinate, squalene and glycyrrhizinate salts. Preferably, the moisturizing agent is a hydrocarbon such as squalene. Preferably, the pH balancer is an amine such as triethanolamine.

An embodiment of the invention provides a composition that can be safely used around the eyes and other sensitive areas of the body including nose, lips and mouth.

An embodiment of the invention provides a composition that can be used on the hair and nails of a human subject in addition to use on the subject's skin.

A six-week clinical trial was conducted to evaluate the safety of a composition of the invention on male and female subjects with sensitive eyes, blepharitis, rosacea or seborreheic dermatitis. Thirty-nine individuals with healthy, non-diseased eyes completed the study. Of the 39 subjects who completed study participation, the listed percentage of subjects had the following characteristics:

Self-Perceived Sensitive Eyes: 39 subjects (100.0%)
History of Blepharitis: 17 subjects (43.6%)
History of Rosacea: 14 subjects (35.9%)
History of Seborreheic Dermatitis: 5 subjects (12.8%)
Contact Lens Wearers: 17 subjects (43.6%)

Subjects applied the test product at least twice per day every day for the duration of the study. Application was performed all over the face of the subjects including the periorbital area (around the eye). Subjects participated in the following procedures at Baseline, Week 3, and Week 6:

Visual Acuity

Clinical staff performed visual acuity tests of subjects' right and left eyes.

Slit Lamp Examination

The Investigator performed slit lamp examinations of subjects' right and left eyes for the following parameters:
  Bulbar conjunctival irritation: hyperemia, edema, erosions, and follicles
  Tarsal conjunctival irritation: hyperemia, edema, erosions, and follicles
  Lacrimation (tearing)
  Surrounding skin irritation (upper eye area and under eye area)
  Degree of lens deposits (contact lens wearers only)

Objective and Subjective Irritation Grading of Periocular Area, Eyelids, and Upper Cheeks The Investigator Graded Objective Irritation (Erythema, Edema, Scaling/Dryness) of the left and right periocular areas, eyelids, and upper cheeks. Subjects assessed subjective irritation (stinging, burning, itching, tightness) of the left and right periocular areas, eyelids, and upper cheeks.

Subjective Irritation Grading of Eye/Eye Area

Subjects rated subjective irritation (stinging, burning, itching, foreign body sensation) of the eye/eye area. If a subject responded positively for subjective sensations, the Investigator attempted to determine the cause (allergies, contact lenses, medical condition, etc.) and whether it was product related.

Subjects completed a Sponsor-provided self-assessment questionnaire regarding the product's performance at Week 3 and Week 6.

Overall, the test product was safe for use by male and female subjects with sensitive eyes, blepharitis, rosacea and/or seborheic dermatitis. Self-assessment questionnaires revealed that the subjects rated the test material very favorably (Table 3).

At Baseline and following three and six weeks of product use, a board certified ophthalmologist performed a slit lamp examination of subjects' right and left eyes for opthalmological irritation and clinical evaluations for objective and subjective irritation of the eyes and eye area. Subjects participated in a visual acuity tests at Baseline, Week 3, and Week 6 (prior to the ophthalmological examinations). Table 2 presents the results of these examinations. Mean values at Week 3 and Week 6 are statistically compared to mean Baseline values for significant differences using a paired t-test at the $p \leq 0.05$ significance level.

TABLE 2

Mean Scores for Ophthalmological Examinations, Clinical Evaluations and Visual Acuity Test (n-39*)

| | Right Eye | | | Left Eye | | |
| --- | --- | --- | --- | --- | --- | --- |
| | Baseline Visit 1 | Week 3 Visit 2 | Week 6 Visit 3 | Baseline Visit 1 | Week 3 Visit 2 | Week 6 Visit 3 |
| SLIT LAMP EXAMINATION | | | | | | |
| Bulbar Conjunctival Hyperemia | 0.08 | 0.00↓ | 0.00 | 0.09 | 0.00 | 0.00 |
| Bulbar Conjunctival Edema | 0.00 | 0.00 | 0.00 | 0.00 | 0.00 | 0.00 |

TABLE 2-continued

Mean Scores for Ophthalmological Examinations, Clinical Evaluations and Visual Acuity Test (n-39*)

|  | Right Eye | | | Left Eye | | |
| --- | --- | --- | --- | --- | --- | --- |
|  | Baseline Visit 1 | Week 3 Visit 2 | Week 6 Visit 3 | Baseline Visit 1 | Week 3 Visit 2 | Week 6 Visit 3 |
| Bulbar Conjunctival Erosions | 0.00 | 0.00 | 0.00 | 0.00 | 0.00 | 0.00 |
| Bulbar Conjunctival Follicles | 0.00 | 0.00 | 0.00 | 0.00 | 0.00 | 0.00 |
| Tarsal Conjunctival Hyperemia | 0.00 | 0.00 | 0.00 | 0.01 | 0.00 | 0.00 |
| Tarsal Conjunctival Edema | 0.00 | 0.00 | 0.00 | 0.00 | 0.00 | 0.00 |
| Tarsal Conjunctival Erosions | 0.00 | 0.00 | 0.00 | 0.00 | 0.00 | 0.00 |
| Tarsal Conjunctival Follicles | 0.00 | 0..03 | 0.00 | 0.00 | 0.03 | 0.00 |
| Lacrimation | 0.05 | 0.05 | 0.03 | 0.05 | 0.05 | 0.03 |
| Upper Eye Area Irritation | 0.46 | 0.00↓ | 0.00↓ | 0.45 | 0.00↓ | 0.00↓ |
| Lens Deposits | 0.43 | 0.29 | 0.23 | 0.47 | 0.33 | 0.14↓ |
| VISUAL ACUITY | 0.93 | 0.93 | 0.90 | 0.91 | 0.94 | 0.89 |
| IRRITATION GRADING OF EYE AND EYE AREA | | | | | | |
| Stinging | 0.24 | 0.05 | 0.08 | 0.24 | 0.05 | 0.08 |
| Burning | 0.26 | 0.00↓ | 0.08 | 0.26 | 0.00↓ | 0.08 |
| Itching | 0.92 | 0.08↓ | 0.14↓ | 0.92 | 0.08↓ | 0.14↓ |
| Foreign Body Sensation | 0.39 | 0.00↓ | 0.10↓ | 0.42 | 0.00↓ | 0.10↓ |
| IRRITATION GRADING OF PERIOCULAR AREA, EYELIDS AND UPPER CHEEKS | | | | | | |
| Erythema | 0.16 | 0.05 | 0.03↓ | 0.16 | 0.05 | 0.03↓ |
| Edema | 0.13 | 0.00↓ | 0.00↓ | 0.13 | 0.00↓ | 0.00↓ |
| Scaling/Dryness | 0.58 | 0.28 | 0.13↓ | 0.58 | 0.28 | 0.13↓ |
| Stinging | 0.05 | 0.11 | 0.08 | 0.05 | 0.11 | 0.08 |
| Burning | 0.05 | 0.05 | 0.03 | 0.08 | 0.05 | 0.03 |
| Itching | 0.29 | 0.11 | 0.06↓ | 0.29 | 0.11 | 0.06↓ |
| Tightness | 0.42 | 0.16 | 0.08↓ | 0.42 | 0.16 | 0.08↓ |

↓Indicates a statistically significant ($p \leq 0.05$) decrease compared to baseline Table 3 presents the results of the self-assessment questionnaire immediately post-application and at Week 2 and Week 4. The number of subjects (and corresponding percentage of the subject population) with the indicated response is listed for each question.-

TABLE 3

Results of Analysis of Self-Assessment Questionnaire

|  | Week 3 | | Week 6 | |
| --- | --- | --- | --- | --- |
|  | Excellent Very Good Good | Poor Very Poor Extremely Poot | Excellent Very Good | Poor Very Poor Extremely Poot |
| Overall performance of product | 29 (76.3%) | 4 (10.5%) | 28 (75.7%) | 4 (10.8%) |
|  | Agree Strongly, Agree Somewhat | Disagree Somewhat, Disagree Strongly | Agree Strongly, Agree Somewhat | Disagree Somewhat, Disagree Strongly |
| Cleanses down to the pores to remove dirt, oil, & make-up | 26 (68.4%) | 6 (15.8%) | 25 (67.6%) | 8 (21.6%) |
| Does not sting or irritate eyes | 33 (86.8%) | 3 (7.9%) | 34 (91.9%) | 1 (2.7%) |
| Suitable to use on the eye area | 35 (92.1%) | 2 (5.3%) | 36 (97.3%) | 1 (2.7%) |
| Velvety cream cleanser | 28 (73.7%) | 2 (5.3%) | 28 (75.7%) | 5 (13.5%) |
| Satiny soft feel | 32 (84.2%) | 1 (2.6%) | 30 (81.1%) | 2 (5.4%) |
| Rinses clean without over-drying or stripping the skin | 31 (81.6%) | 5 (13.2%) | 32 (86.5%) | 3 (8.1%) |
| Cleanses without over drying the skin | 31 (81.6%) | 4 (10.5%) | 32 (86.5%) | 5 (13.5%) |
| Suitable for all skin type including sensitive skin | 31 (81.6%) | 4 (10.5%) | 32 (86.5%) | 4 (10.8%) |
| Sweeps away dulling skin cells | 21 (55.3%) | 7 (18.4%) | 21 (56.8%) | 7 (18.9%) |
| Won't clog pores | 27 (71.1%) | 2 (5.3%) | 25 (67.6%) | 5 (13.5%) |

TABLE 3-continued

Results of Analysis of Self-Assessment Questionnaire

|  | Week 3 | | Week 6 | |
| --- | --- | --- | --- | --- |
| Non-irritating | 35 (92.1%) | 2 (5.3%) | 33 (89.2%) | 2 (5.4%) |
| Gentle for daily use | 35 (92.1%) | 2 (5.3%) | 34 (91.9%) | 2 (5.4%) |
|  | No | Yes | No | Yes |
| Did you experience any irritation using this product? | 32 (84.2%) | 6 (15.8%) | 33 (89.2%) | 4 (10.8%) |
|  | None | Mild, Moderate, Severe | None | Mild, Moderate, Severe |
| If yes, please describe the level of irritation | 0 (0.0%) | 6 (100.0%) | 0 (0.0%) | 4 (100.0%) |

What is claimed is:

1. A composition for the treatment of skin conditions, consisting of:
    from 0.005% to 1% by weight of an admixture containing: an extract of *Bambusa vulgaris*, an extract of *Pisum sativum*, and glucosamine hydrochloride;
    from 0.05% to 5% by weight of tetrahexyldecyl ascorbate;
    from 2% to 10% by weight of butylene glycol;
    from 0.05% to 5% by weight of xanthan gum;
    from 0.05% to 5% by weight of a methyl paraben;
    from 0.05% to 5% by weight of dipotassium glycyrrhizinate;
    optionally from 0.05% to 5% by weight of an emulsifier;
    from 5% to 30% by weight squalene;
    from 0.05% to 5% by weight of a propylparaben: and
    the balance water.

2. The composition according to claim 1, wherein
    the concentration of tetrahexyldecyl ascorbate is 0.5% by weight; and
    the concentration of dipotassium glycyrrhizinate is 1% by weight.

\* \* \* \* \*